United States Patent [19]

Devanaboyina

[11] Patent Number: 5,571,114

[45] Date of Patent: Nov. 5, 1996

[54] MECHANISM TO ADVANCE OR WITHDRAW OBJECTS IN LUMENS OR CAVITIES OF MAMMALS

[76] Inventor: Udaya-Sankar Devanaboyina, 12646 Monterey Cypress Way, San Diego, Calif. 92130

[21] Appl. No.: 274,340

[22] Filed: Jul. 13, 1994

[51] Int. Cl.$^6$ .................................................. A61B 1/00
[52] U.S. Cl. .................................... 606/108; 606/1
[58] Field of Search .................... 606/108–159, 606/167, 168, 169, 170, 177, 178, 179; 604/264, 280, 164; 128/749, 755, 757, 772

[56] References Cited

U.S. PATENT DOCUMENTS 4,798,193  1/1989  Giesy et al. ........................ 606/108

*Primary Examiner*—Robert A. Hafer
*Assistant Examiner*—Benjamin Koo
*Attorney, Agent, or Firm*—Dennis H. Rainear

[57] ABSTRACT

The invention provides a mechanism for an improved medical or veterinary implement comprising a chain or sheath covering an elongated tool or instrument. The sliding sheath of the invention helps the process of insertion and advancement of the implement into a lumen and reduces the friction and pressure induced on the side walls of the lumen into which the sheathed implement is inserted for purposes of treatment or examination.

20 Claims, 3 Drawing Sheets

MECHANISM TO ADVANCE OR WITHDRAW OBJECTS IN LUMENS OR CAVITIES OF MAMMALS

TECHNICAL FIELD

The present invention relates to a mechanism useful as a medical or veterinary implement to facilitate the insertion and advancement of an instrument into the lumens of a mammal without causing damage or irritation of the lumen walls. The instrument with the inventive mechanism can be a device such as an endoscope, catheter, guide wires, feeding tubes, drug delivery systems, micromachines, and the like useful for diagnostic or therapeutic purposes.

BACKGROUND ART

The endoscopic examination of internal regions and organs of the body of a mammal is often used to diagnose or treat disease conditions. The modern fibro-optic endoscopes are very flexible and offer little resistance to the curves of the lumen. However, when deeper sites of the long lumens are to be reached, some of the loops in the proximal region of the lumen receive more pressure on their walls which makes it difficult for the endoscope to be pushed forward. This may lead to unwanted complications and incomplete endoscopic examination. As a result, most of the prior art endoscopes cannot be advanced manually by pushing forward in the intestines.

Previous fiber-optic endoscope systems include the charge coupled device and the electronic video endoscopy.

Microvasive Boston Scientific Corporation produces an imaging device for flexible endoscopy called the EndoSound Endoscopic Ultrasound Catheter. However, its flexible shank needs considerable maneuvering to introduce it into the lumen.

Fujinon (Europe) GmbH, Germany, produces a series of fibre-optic endoscopes including ADAM (Advanced Digitizing And More) and EVE (Electronic Video Endoscopy), however these also suffer from the difficulties of insertion, manipulation, and withdrawal.

Olympus Optical Company, (Europa) GmbH, Germany, produces a flexible endoscope called the EVIS 100 and another called the OLYMPUS Mother-Babyscope.

Olympus Corporation, Lake Success, N.Y. produces several designs of Sonde Enteroscopes that include SIF-SW and SSIF-VI. These fiberoptic designs are advanced passively into the distal small bowel by the small bowel motility. These prototypes lack both tip control and therapeutic channels, precluding the ability to visualize the entire mucosa and to either treat or mark the suspected area of bleeding once found.

Pentax Medical Division, Pentax Handelsgesellschaft mbH, Germany, produces an endoscope with high suction capacity, but which cannot reduce friction or pressure on the lumen walls and also presents problems while being advanced in the lumen.

Pentax Precision Instrument Corporation, Orangeburg, N.Y. has developed a series of small bowel video endoscopes, however, these require mandatory use of a fluoroscopy and an overtube. It also requires considerable amount of lubricants to reduce friction while inserting the endoscope into the overtube.

Catheters are used very often either to diagnose conditions related to circulatory system such as angiography, and to institute treatment, or for surgical interventions or simply to provide drainage through a blocked urethra. Since most catheters are made of pliable material, guide wires are usually employed to provide stiffness and to push them forward in the lumen. This can create a frictional force sufficient to injure the endothelium of the lumen resulting in complications such as thrombosis and perforation. Therefore, it would be desirable to have a catheter that can effectively be introduced to a lumen with minimal trauma to the endothelium of the lumen.

It would therefore be desirable to have an implement which is not only flexible, but which is modified to reduce or eliminate friction and excess pressure on the walls of the lumen and able to reach the site of interest without a lot of difficulty during diagnostic or therapeutic treatment.

BRIEF DISCLOSURE OF INVENTION

The present invention is directed to a sliding mechanism on medical or veterinary implements, said sliding mechanism being useful in extending the reach and view while reducing the adverse effects on the patient due to tissue injury. The present invention can be used in the examination or treatment of humans or animals.

Thus, one object of the present invention is to present a sheathed, linked or chained medical or veterinary implement comprising:

a) an elongated body having a first end and a second end;

b) at least one sliding sheath comprising a loop of film, chain or linked material, said sheath being positioned parallel said elongated body and wherein the sheath loop consists of an inner section and a parallel outer section;

c) a first means for anchoring each sheath to a position on the elongated body near the first end of the elongated body, whereby the outer section of the sheath can pass around said first anchoring means, reverse direction to form the inner section, said inner section being free to slide along the elongated body;

d) a second means for anchoring the sheath to a position on the elongated body some distance removed from the first end of the elongated body, whereby the inner section of the sheath can pass around said second anchoring means and reverse direction to form the outer section;

whereby when the elongated body is advanced into a lumen, the outer section of the sheath contacts a side wall of the lumen and passes around the first and second anchoring means thereby giving support for the forward movement of the endoscope, while reducing the friction on said lumen side wall.

In one embodiment of the present invention, an elongated implement, such as for example, an endoscope or catheter, is provided which is covered in at least one sheath or chain or outer casing of a thin and tough film. Preferably, this chain or sheath is a two layered film which is constructed as a loop, whereby a first outer section of the loop slides over the second inner section of the loop. Thus, "sheath" or "sheath loop" herein shall mean any continuous film, chain, linked, hinged or beaded means capable of changing position relative to an underlying endoscopic tool, whereby the endoscopic tool can more easily advance within a lumen. An example of this loop would be the conveyor belt, tractor tread, or caterpillar wheel often used on a military tank or other heavy equipment. Another example of the sheath or sheath loop useful in the present invention is a chain or multilinked mechanism. Thus the word "chain" can be substituted herein for "loop" or "sheath".

The sheath loop can be positioned between two or more posts, hoops, or wickets or other anchoring means, around or through which the sheath loop passes and then circles back on itself to complete a circle. The anchoring means does not prevent the movement or sliding of the sheath. In addition or in the alternative, a set of wheels, gears, rollers or other rotational device can be positioned near a first tip of the elongated implement to improve entry and forward movement into the lumen by allowing the film sheath, such as a chain, to ride over and rotate said wheels, gears or rollers. As the elongated body or shank of the device or implement is advanced into the lumen, the first outer section of the looped film sheath or chain, in addition to the implement itself, touches and maintains contact with the walls of the lumen, and said looped film sheath or chain advances or rotates over the wheel or other anchoring device while the second inner section of the looped film sheath slides beneath the first section and along the elongated body or shank of the implement. The looped film sheath, having contacted the lumen wall, remains stationary with regard to the wall, while the implement is advanced. The sheath loop is thereby "walked" into the lumen rather than dragged. The first outer section of the looped film sheath touches and maintains contact with the walls of the lumen without having to slide or drag over, across or along the tissue. In this manner, the friction and pressure created upon the walls or endothelium of the lumen during insertion, advancement and removal of the implement can be significantly reduced, relative to the friction and discomfort and endothelium damage experienced with conventional, non-sheathed implements. As the driving wheels rotate, the chain is moved from inside to outside, thereby extending the length of the chain at the advancing end. Multiple driving wheels or chains placed along the length of the endoscope tube can be used to bring about desired uniform distribution of pulling force and the desired effect. To accommodate the increase in length of the chain, the advancing end the endoscope will be forced to move in the forward direction or backward direction depending on the direction of the wheel rotation. The chain described herein could be a part of the film sheath that encircles the endoscope. In such a case, the first outer section of the sheath which comes into contact with the cells that line the lumen which is being examined does not move, relative motion between the sheath and the lining epithelium would be completely eliminated by the present invention. The outer sheath also prevents direct contact between the shank of the implement and the lining epithelium, thereby minimizing damage to the lining epithelium from friction created by movement of the implement within the lumen.

By "implement" or "device" herein is meant any medical or veterinary device, instrument, article, or tool, of a tubular or elongated shape, which is used to treat or examine an orifice, canal, lumen or cavity of a mammal. Examples of such implements or devices include, but are not limited to, endoscopes, catheters, optofibers, guide wires, feeding tubes, drug delivery systems, micromachines, and the like. The implement or device of the present invention also includes the article produced by retrofitting a conventional implement or device with an attachable modification as described herein and comprising the sheath and anchoring means of the present invention.

By "endoscope" herein is meant any device, article, instrument, or tool used by medical or veterinary doctors or technicians for the examination or treatment of orifices, cavities, canals, lumen, and the like. Thus, for example, and not by way of limitation, included as endoscopes herein are colonoscopes, bronchoscopes, uteroscopes, pancreatoscopes, enteroscopes, gastroscopes, angioscopes, fibroscopes, videoendoscopes, endoscopes, and the like.

By "lumen" herein are meant any and all mammalian body cavities, such as but not limited to, colon, duodenum, esophagus, trachea, bronchii, stomach, lungs, arteries, veins, capillaries, vagina, uterus, gall bladder, ureters, kidneys, peritoneal and thoracic cavities, synovial spaces, spinal cord cavity, urethra, ducts, and organs such as eye and heart and the like.

BRIEF DESCRIPTION OF DRAWINGS

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose.

DETAILED DESCRIPTION

Figure 1:
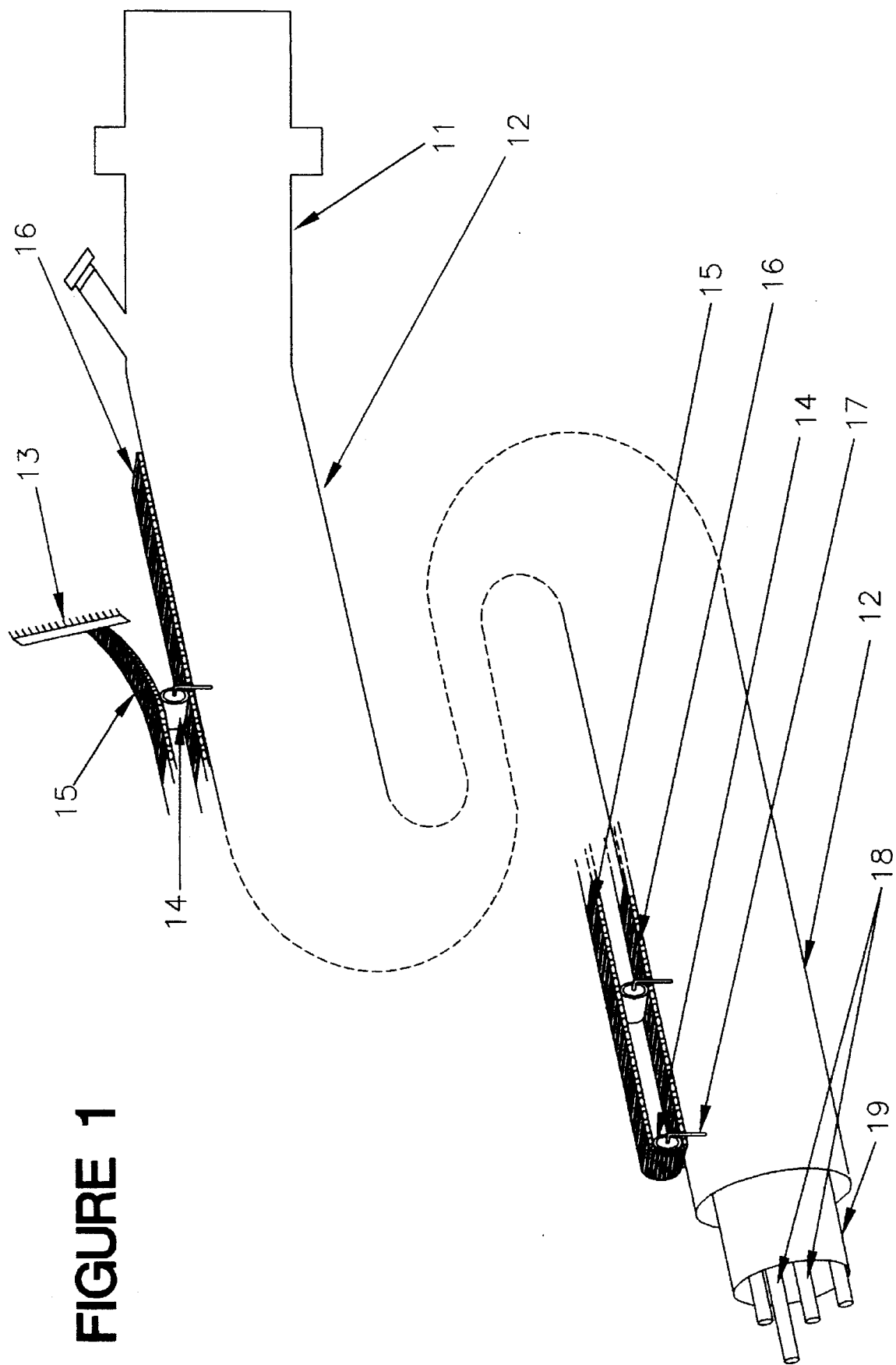
FIG. 1 depicts a sheathed or chained implement of the present invention.

Thus, in one embodiment of the present invention, a modified and improved medical or veterinary implement is presented, wherein the elongated body of the implement is an endoscope which comprises a fibro-optic or electrical member which includes a flexible chain, sheath or film covering attached in a folded or looped manner via an anchoring system to a cable or fiber capable of transmitting electrical or optical signals, whereby the anchoring system, such as a wheel, gear, hoop, ring or a post, (also referred to herein as a "wicket") allows the chain or sheath to slide along the length of the transmitting cable or fiber. The transmitting cable can be any material, such as for example, glass fiber, capable of transmitting an image or signal. Thus by "transmitting" herein is meant any visible or electronic signal which can ultimately be read or viewed in digital, analog, three dimensional holographic, or two dimensional visual form. The sliding sheath revolves, rotates or loops around or over the anchoring system as the endoscopic light transmitting cable beneath is advanced in the lumen. In a preferred embodiment, the anchoring system further comprises a wheel, sprocket, roller, or other circular or cylindrical device over which the chain or sheath can ride, thereby forming a loop end and allowing the sheath to reverse direction back alongside the side or shank of the endoscope, thereby defining a first outer section of the loop and a second inner section of the loop.

The chain or sheath is, in one embodiment, attached to the elongated body of the implement such as a transmitting cable or fiber at or near the distal end of a light transmitting cable and also at another second point along the length of the light transmitting cable. The second point of attachment of the sliding sheath, via wheels, rollers or an anchoring post, can be at or near the proximal end of the endoscope, or at any desired length from the distal end, depending on the length of the lumen, organ or cavity being examined or treated.

In one embodiment of the present invention, one end of the chain or sheath lies on or adjacent the shank of the implement and is fed from a reel that lies outside the body, near the proximal end of the insertion tube. As the implement is advanced into the lumen, the chain or sheath is pulled forward onto the shank, thereby ensuring continuous supply of the chain or sheath.

A sliding sheath can be added onto the endoscope containing a chain to thereby further reduce trauma to the lumen. The sliding sheath is also anchored in a manner similar to the anchoring of the chain and works similarly to the chain.

The film sheath used in the present invention to cover the implement for easier insertion into the lumen can be smooth, or exhibit ridges to achieve desired traction within certain organs or openings. In one embodiment, the film sheath is removable and replaceable so that the physician can change from a smooth sheath to one with improved traction, depending on the tissue texture and lubricity. The traction or tread pattern on the film sheath can be parallel or perpendicular to the length of the sheath loop, or the tread can be an alternate design shape, such as cross hatched or diamond shaped pattern.

The chain material useful in the present invention can be any firm, non-toxic material, including metal such as iron, copper, aluminum, titanium, stainless steel, alloys or mixtures thereof, or ceramic composite materials or plastics.

The film sheath material is preferably but not limited to a synthetic polymer or copolymer material selected from the group consisting of polyvinyl chloride, polyethylene, polypropylene, polybutadiene, polyester, nylon, and the like, and blends and copolymers thereof.

The film sheath useful herein can be either impermeable to liquids or porous, or permeable to allow for exchange of liquids, solutes, and gases. Such permeability may in some situations be helpful in maintaining tissue nutrition, hydration and oxygenation or for drug or food delivery to a localized area. This is especially useful in the case of catheters.

The outer or the inner section of the film sheath can also have the capability of being inflated and deflated (similar to balloons) at selected locations, to permit the anchoring of the implement in the lumen or for other purposes.

The film sheath can be of variable thickness, but thin film sheaths are preferred herein in order to (1) minimize total diameter of the sheathed endoscope, and (2) improve the ability of the film sheath to rotate around the wheels or anchoring posts.

Several driving devices can be utilized on the implement to pull the endoscope into the lumen, using the chain or sheath. A variety of conventional battery-powered or electrical and mechanical systems can be used to accomplish the task. The driving devices can be, for example and not by limitation, conventional rotational devices, motors, servomotors, or micromachines, or engines placed near the tip or at various points along the shank or elongated body of the implement to rotate the chain, or various mechanical or hydraulic or pneumatic systems placed within the endoscope or other implement near its tip to move the implement forward.

Thus, in FIG. 1 is depicted an example of the present invention wherein the elongated body is an endoscope 11 with a chain 15 and 16, said chain 15 and 16 being attached at the distal end of the endoscope 11 by means of an anchoring hoop or ring 17. The anchoring hoop or ring 17 may optionally hold a wheel, sprocket, or other circular or cylindrical device 14 which can rotate around or on said anchoring hoop or ring 17 and over which the chain 15 and 16 can pass. The rotational device 14 makes said chain 15 and 16 move forward or backward. The chain 15 and 16 forms a long loop lying over and alongside the elongated body or light transmitting cable 12 of the endoscope 11 with the ends of the loop being formed around the rotational device 14. One end of the chain 15 is anchored to a post 13 located at some desired distance from the distal end 19 of the light transmitting cable 12. The chain thus comprises an outer section 15 which contacts the lumen wall and an inner section 16 which is close to the implement shank 12. The endoscope 11 can optionally contain a biopsy illuminator fiber bundle 18 and/or a suction channel 18.

Depending on the diameter of the implement and the lumen to be examined or treated, the implement of the present invention can be equipped with one or more chains or sheaths at different sites on the shank 12. As the number of chains or sheaths on the shank of the implement 12 increases, the maneuverability of the implement is improved. Thus a device of the present invention can include multiple chains or sheaths 15 and 16 on the elongated implement 12.

The anchoring means utilized in the present invention need not be limited to two locations. It is also useful herein to utilize a plurality of anchoring means in combination. As described above, the anchoring means can be equipped with drive mechanisms to further facilitate ease of implement insertion.

Figure 2:
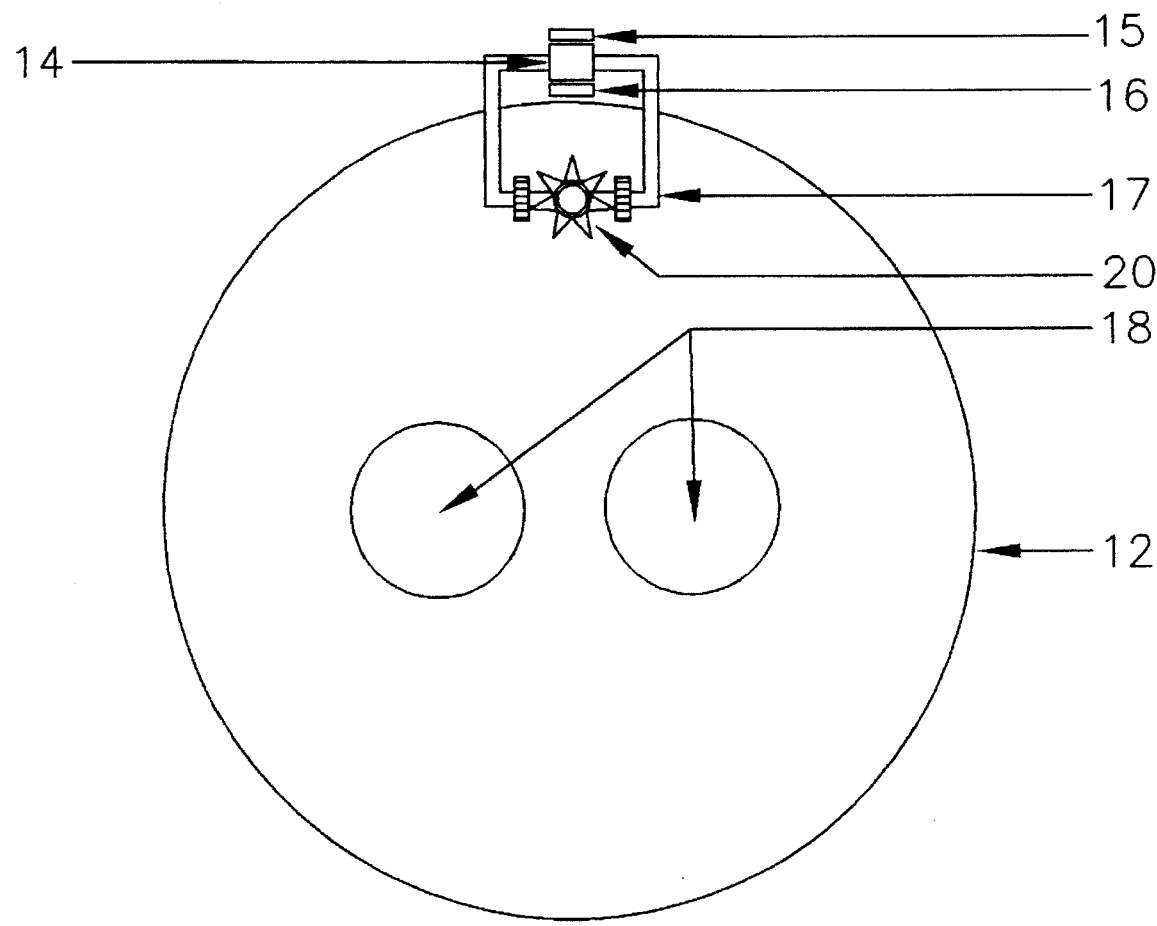
FIG. 2 depicts a cross section view of a sheathed or chained implement of the present invention.

FIG. 2 illustrates a cross sectional view of the instrument described in FIG. 1. The chain 15 and 16 is driven by the rotational device 14 anchored to post 17. The driving force is provided by a flexible shaft 20 that runs along the length of the endoscope shank 12. Several alternative devices can be used to run the rotational devices in addition to the flexible cable.

Figure 3:
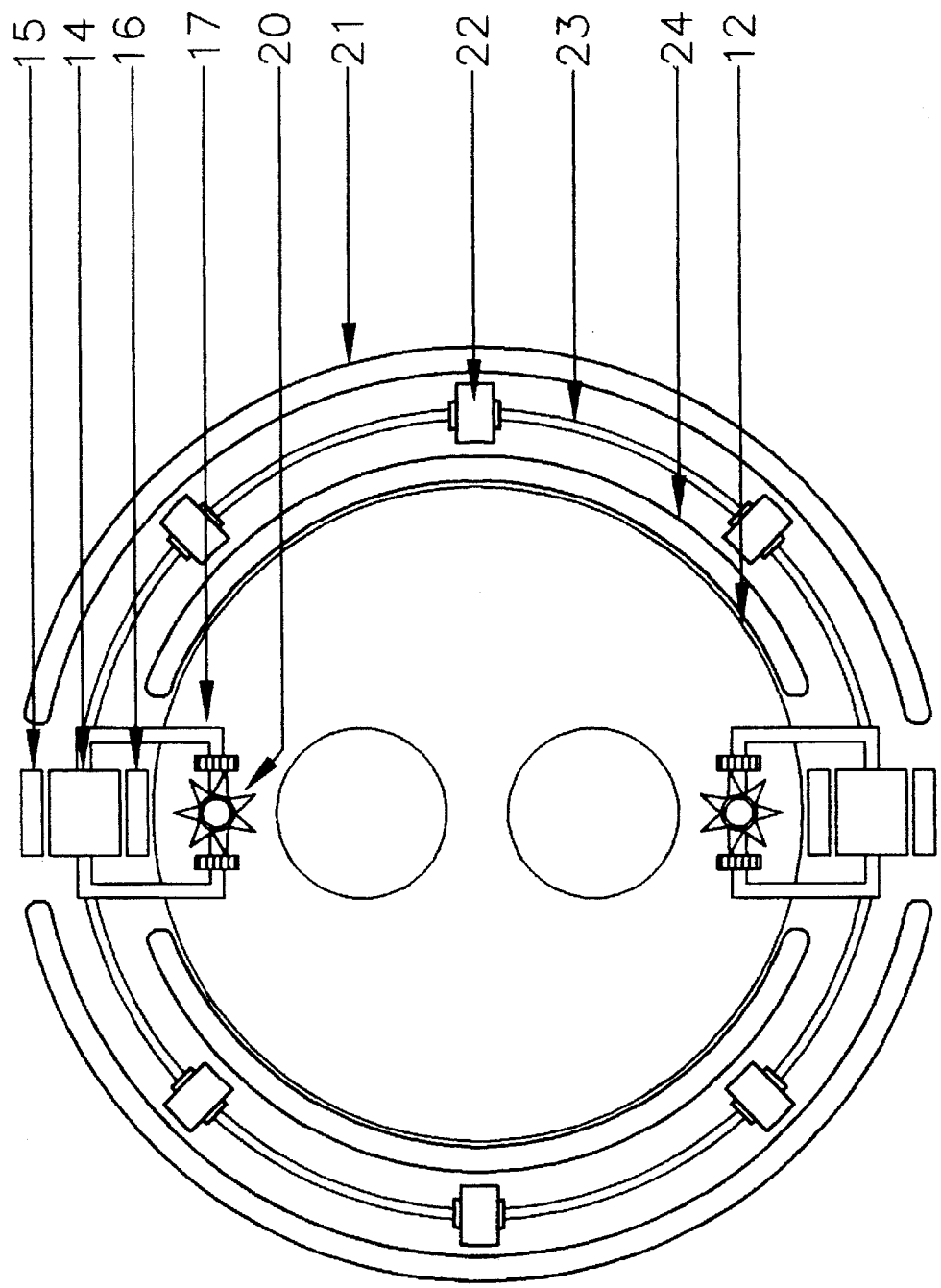
FIG. 3 depicts a cross sectional view of a chained implement of the present invention containing a sliding sheath.

More than one driving chain can be used to advance the instrument. To reduce the frictional force on the luminal wall, a sliding sheath can also be used in addition to the driving chain as shown in FIG. 3. The embodiment in FIG. 3 comprises an outer sheath of film 21, anchored to a post 13 similar to the chain 15 in FIG. 1. The sheath passes over the rotational devices 22 placed on a supporting rotational axis 23 that can support and/or rotate the sheath. The inner sheath 24 passes along the body of the insertion tube 12, similar to the driving chain 16. The outer sheath lines the lumen wall as the endoscope moves forward thereby reducing trauma to the lumen.

One embodiment of the present invention comprises a chain or thick sheath in addition to the thin sheath that rolls around the endoscope as has been described. One end of the chain that lies adjacent to the lumen wall (i.e., the outer chain) is anchored to a fixed support, while the other end is free. Both segments of the chain can be covered by a tube or a groove to hold the chain in position. As the driving wheels rotate, the inner chain is drawn forward and pushed outward. However, since the outer chain is anchored to a fixed support, the outward movement of the inner chain would stop, unless the endoscope moves forward to make space for the movement of the inner chain. The outer segment of the chain provides support for the endoscope to move forward. This is very similar to rack and pinion movement; the outer sheath serves as a rack and the driving wheel with the attached endoscope move forward or backward like a pinion.

Another embodiment of the present invention utilizes as the elongated body of the implement a catheter useful for examining and/or treating a mammalian lumen. Thus, for example, vascular, cardio, gastrointestinal, uterine or urethral catheters can be equipped with the sliding sheath and/or chain mechanism of the present invention to reduce friction, minimize endothelium trauma, and increase patient comfort during examination or treatment. There is no known upper or lower limitation on the length or diameter of the improved, sheathed implement of the present invention. Thus, microoptical fibers equipped with one or more sliding sheaths of the present invention are useful for the examination and treatment of small veins, arteries, bronchial tubes and the like.

Another object of the present invention is an improved method for reducing patient trauma while examining or treating a lumen of said patient, said method comprising advancing into a lumen of a mammal a medical or veterinary implement comprising a) an elongated means having a first end and a second end;
 b) at least one chain or sheath comprising a loop of material, said sheath being positioned parallel said elongated means and wherein the sheath loop consists of an inner section and a parallel outer section;
 c) a first means for anchoring each chain or sheath to a position on the elongated means near the first end of the elongated means, whereby the outer section of the sheath can pass around said first anchoring means, reverse direction to form the inner section, said inner section being free to slide along the elongated means;
 d) a second means for anchoring the sheath to a position on the elongated means some distance removed from the first end of the elongated means, whereby the inner section of the sheath can pass around said second anchoring means or a rotational device and reverse direction to form the outer section;

whereby when the elongated means is advanced into a lumen, the chain or sheath contacts a side wall of the lumen and passes around the first anchoring means thereby reducing the friction on said lumen side wall and reducing patient trauma, relative to the patient trauma experienced without said chain or sheath on the elongated means.

In another embodiment of the present invention, the endoscope can be equipped with an inflatable sheath that can fill or partially fill the space between the endoscope and the lumen wall after the sheath passes through the driving wheels. This will provide good support for the forward motion of the endoscope. Such an inflatable sheath could be used in combination with a pneumatic or hydraulic pump and the driving wheels or gears.

In yet another embodiment, the sheathed or chain-equipped endoscope of the present invention is provided as an attachment or extension to be connected to another endoscope, whereby the end portion of the inserted instrument has improved insertion with reduced patient trauma, relative to an endoscope without the attachment of the present invention. In a preferred embodiment, this inventive extension snaps onto a conventional endoscope using snaps known in the art.

While certain preferred embodiments of the present invention have been disclosed in detail, it is to be understood that various modifications may be adopted without departing from the spirit of the invention or scope of the following claims.

I claim:

1. A sheathed medical or veterinary implement comprising:

a) an elongated body having a first end and a second end;
 b) at least one sheath comprising a loop of film material, said sheath being positioned parallel said elongated body and wherein the sheath loop consists of an inner section and a parallel outer section;
 c) a first means for anchoring each sheath to a position on the elongated body near the first end of the elongated body, whereby the outer section of the sheath can pass around said first anchoring means, reverse direction to form the inner section, said inner section being free to slide along the elongated body;
 d) a second means for anchoring the sheath to a position on the elongated body some distance removed from the first end of the elongated body, whereby the inner section of the sheath can pass around said second anchoring means and reverse direction to form the outer section;

whereby when the elongated body is advanced into a lumen, the sheath contacts a side wall of the lumen and passes around the first anchoring means thereby reducing the friction on said lumen side wall.

2. The sheathed implement of claim 1 wherein the film material is selected from the group consisting of polyvinyl chloride, polyethylene, polypropylene, polybutadiene, polyester, nylon, blends, mixtures, and copolymers thereof.

3. The sheathed implement of claim 1 wherein the chain material is a chain made of a material selected from the group consisting of iron, copper, titanium, stainless steel, aluminum, alloys thereof, ceramic composites, and plastic.

4. The sheathed implement of claim 1 wherein at least one of the anchoring means further comprises a rotational device over which the sheath makes contact causing the rotational device to rotate when the outer section of the sheath contacts the side walls of the lumen.

5. The sheathed implement of claim 1 wherein the implement has a plurality of sheaths.

6. The sheathed implement of claim 1 wherein the elongated body is selected from the group of endoscopes consisting of colonoscopes, bronchoscopes, uteroscopes, pancreatoscopes, catheters, enteroscopes, gastroscopes, angioscopes, fibroscopes, videoendoscopes, and other endoscopes.

7. The sheathed implement of claim 1 wherein the elongated body is selected from the group consisting of catheters, guide wires, micromachines, optofibers, feeding tubes, and drug delivery systems.

8. The sheathed implement of claim 1 wherein the anchoring means further comprises a driving device capable of advancing the film sheath, said device selected from the group consisting of servo-motors, engines, motors, and micromachines.

9. An improved method for reducing patient trauma while examining or treating a lumen of said patient, said method comprising advancing into a lumen of a mammal a medical or veterinary implement comprising a) an elongated body having a first end and a second end;
 b) at least one sheath comprising a loop of film material, said sheath being positioned parallel said elongated body and wherein the sheath loop consists of an inner section and a parallel outer section;
 c) a first means for anchoring each sheath to a position on the elongated body near the first end of the elongated body, whereby the outer section of the sheath can pass around said first anchoring means, reverse direction to form the inner section, said inner section being free to slide along the elongated body;
 d) a second means for anchoring the sheath to a position on the elongated body some distance removed from the first end of the elongated body, whereby the inner section of the sheath can pass around said second anchoring means and reverse direction to form the outer section;

and when the elongated body is advanced into said lumen, reducing the friction on an inner side wall of said lumen and reducing patient trauma by contacting the lumen side wall with the outer section of the sheath.

10. The method of claim 9 wherein the film material is selected from the group consisting of polyvinyl chloride, polyethylene, polypropylene, polybutadiene, polyester, nylon, blends, mixtures, and copolymers thereof.

11. The method of claim 1 wherein the film material is a chain made of material selected from the group consisting of iron, copper, titanium, stainless steel, aluminum, alloys thereof, ceramic composites, and plastics.

12. The method of claim 9 wherein at least one of the anchoring means further comprises a rotational device over which the sheath makes contact causing the rotational device to rotate when the outer section of the sheath contacts the side walls of the lumen.

13. The method of claim 9 wherein the implement has a plurality of sliding sheaths.

14. The method of claim 9 further comprising additional anchoring means.

15. The method of claim 9 wherein the elongated body is selected from the group of endoscopes consisting of colonoscopes, bronchoscopes, uteroscopes, pancreatoscopes, catheters, enteroscopes, gastroscopes, angioscopes, fibroscopes, videoendoscopes, and other endoscopes.

16. The method of claim 9 wherein the elongated body is selected from the group consisting of catheters, guide wires, micromachines, optofibers, feeding tubes, and drug delivery systems.

17. The method of claim 9 wherein the anchoring means further comprises a driving device capable of advancing the film sheath, said device selected from the group consisting of servo-motors, engines, motors, and micromachines.

18. A sheathed medical or veterinary implement comprising:

a) an elongated body having a first end and a second end;

b) at least one sheath comprising a loop of chain material, said sheath being positioned parallel said elongated body and wherein the sheath loop consists of an inner section and a parallel outer section;

c) a first means for anchoring each sheath to a position on the elongated body near the first end of the elongated body, whereby the outer section of the sheath can pass around said first anchoring means, reverse direction to form the inner section, said inner section being free to slide along the elongated body;

d) a second means for anchoring the sheath to a position on the elongated body some distance removed from the first end of the elongated body, whereby the inner section of the sheath can pass around said second anchoring means and reverse direction to form the outer section;

whereby when the elongated body is advanced into said lumen, the sheath contacts an inner side wall of the lumen and passes around the first anchoring means thereby reducing the friction on said lumen side wall.

19. An improved method for reducing patient trauma while examining or treating a lumen of said patient, said method comprising advancing into a lumen of a mammal a medical or veterinary implement comprising a) an elongated body having a first end and a second end;

b) at least one sheath comprising a loop of chain material, said sheath being positioned parallel said elongated body and wherein the sheath loop consists of an inner section and a parallel outer section;

c) a first means for anchoring each sheath to a position on the elongated body near the first end of the elongated body, whereby the outer section of the sheath can pass around said first anchoring means, reverse direction to form the inner section, said inner section being free to slide along the elongated body;

d) a second means for anchoring the sheath to a position on the elongated body some distance removed from the first end of the elongated body, whereby the inner section of the sheath can pass around said second anchoring means and reverse direction to form the outer section;

and when the elongated body is advanced into said lumen, reducing the friction on an inner side wall of said lumen and reducing patient trauma by contacting said inner side wall of said lumen with the outer section of the sheath.

20. A method for advancing or withdrawing implements in lumens or cavities of mammals, said method comprising inserting and advancing into a lumen or cavity of a mammal an implement as claimed in claim 1.

* * * * *